United States Patent
Estes et al.

(10) Patent No.: US 8,711,344 B1
(45) Date of Patent: Apr. 29, 2014

(54) METHOD FOR REMOTELY MEASURING FLUCTUATIONS IN THE OPTICAL INDEX OF REFRACTION OF A MEDIUM

(75) Inventors: Lee E. Estes, Mattapoisett, MA (US); Peter J. Hendricks, Portsmouth, RI (US); Adam Jilling, Portsmouth, RI (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 223 days.

(21) Appl. No.: 13/292,379

(22) Filed: Nov. 9, 2011

(51) Int. Cl.
*G01N 21/41* (2006.01)

(52) U.S. Cl.
USPC .......................................... 356/128

(58) Field of Classification Search
USPC .................. 356/445–448, 364–370
See application file for complete search history.

(56) References Cited

U.S. PATENT DOCUMENTS

| | | | | |
|---|---|---|---|---|
| 4,195,931 A * | 4/1980 | Hara | ............................ | 356/454 |
| 5,074,666 A * | 12/1991 | Barnes et al. | ................. | 356/517 |
| 5,426,505 A * | 6/1995 | Geiser et al. | .................. | 356/517 |
| 5,574,562 A * | 11/1996 | Fishman et al. | .............. | 356/432 |
| 6,175,416 B1 * | 1/2001 | Maris et al. | .................... | 356/630 |
| 6,218,194 B1 * | 4/2001 | Lyndin et al. | ................. | 436/518 |
| 7,789,910 B2 * | 9/2010 | Knox et al. | ................... | 623/6.56 |
| 2010/0253911 A1 * | 10/2010 | Holley et al. | ................ | 351/221 |

OTHER PUBLICATIONS

Fante, Ronald, Electromagnetic Beam Propagation in Turbulent Media, 1975, IEEE vol. 63 p. 1 & 6.*

* cited by examiner

*Primary Examiner* — Gregory J Toatley
*Assistant Examiner* — Maurice Smith
(74) *Attorney, Agent, or Firm* — James M. Kasischke; Michael P. Stanley

(57) ABSTRACT

A method is provided for remotely measuring index of refraction fluctuations. From a first location, an optical beam is focused at a focal plane located at a second location in a medium of interest. As a result, a beam of energy is backscattered towards the first location. At the first location, a size of the backscattered beam is determined where the size is indicative of strength of fluctuations in the medium's index of refraction.

15 Claims, 4 Drawing Sheets

US 8,711,344 B1

METHOD FOR REMOTELY MEASURING FLUCTUATIONS IN THE OPTICAL INDEX OF REFRACTION OF A MEDIUM

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION (1) Field of the Invention

The present invention relates generally to methods for measuring index of refraction, and more particularly to a method for remotely measuring fluctuations in a medium's index of refraction.

(2) Description of the Prior Art

Index of refraction, n, is defined as the ratio between the speed of light in vacuum, c, and the speed of light in a propagation medium, v. When a light source is activated, light propagates from the source at a velocity of 299,792,458 meters per second in a vacuum. Because the speed of light is regarded as a universal constant, the travel time of light is often used as a measurement of distance in terminology such as "light year" and "light second". Light from a laser propagates in a single direction forming a beam and may be pulsed having a pulse duration as short as 10 femtoseconds. Such a pulsed beam has a physical length or extent in space. This physical length can be estimated as the pulse duration multiplied by the speed of light in vacuum. The length can be calculated exactly by multiplying by the speed of light in the medium; however, the speed of light in the medium may not be exactly known.

Measurement of the index of refraction of a light propagation medium is traditionally accomplished by collecting samples of the medium and using instruments such as an optical interferometer or refractometer to measure the index of refraction. Another approach involves measurement of quantities such as temperature, salinity, and pressure, and then using such quantities in analytical models to calculate the index of refraction. While various methods/instruments (e.g., shadowgraphs and wavefront sensors) have been used to indicate the existence of index of refraction fluctuations, these methods/instruments do not have the ability to remotely sense index of refraction fluctuations.

SUMMARY OF THE INVENTION

Accordingly, it is an object of the present invention to provide a method for remotely measuring index of refraction fluctuations.

In accordance with the present invention, a method is provided for remotely measuring fluctuations in a medium's index of refraction. From a first location, a first beam of optical energy is focused at a focal plane located at a second location in a medium of interest. As a result, a second beam of optical energy is backscattered towards the first location. At the first location, a size of the second beam is determined where the size is indicative of strength of fluctuations in the medium's index of refraction.

BRIEF DESCRIPTION OF THE DRAWINGS

Other objects, features and advantages of the present invention will become apparent upon reference to the following description of the preferred embodiments and to the drawings, wherein corresponding reference characters indicate corresponding parts throughout the several views of the drawings and wherein.

DESCRIPTION OF THE INVENTION

The present invention is a novel method for remotely measuring index of refraction fluctuations in a light propagation medium. The present invention takes advantage of some basic principles governing the interaction of a laser beam with a medium. Briefly, when a laser beam is focused in a medium such as water or air, index of refraction variations or fluctuations within the medium can steer the beam, change the divergence of the beam, and break up the beam. Depending on the strength, scale, and range of the index of refraction fluctuations, the size of the beam at the intended focal point (or region) can be significantly larger than the diffraction limited spot size. To measure the size of the beam at the intended focal point, an image of the focused spot can be made at the source of the laser beam by using light that is backscattered from suspended particles and molecular fluctuations within the medium. The image formed is further increased in size as the backscattered light propagates back through the index of refraction fluctuations on the return path. The present invention uses this change in beam size in determining index of refraction fluctuations as will be described below.

In order to capture just a "snapshot" of the region of interest, a variety of well-known optical techniques can be employed. For example, light from the focal point can be isolated by using a pulsed laser beam whose "on" time is short enough so that its extent in space is less than or equal to the depth of focus range. The "on" time is the pulse duration, and the extent in space or length can be estimated by multiplying the pulse duration by the speed of light, c. By time gating the received signal to match the travel time of the light to and from the focal point, the light scattered within the focal volume is further isolated. Measurements of the size of the resulting image are processed in accordance with the present invention to produce a measure of the index of refraction fluctuations encountered during the forward and reverse (i.e., backscattered) propagation of the light beam.

Figure 1:
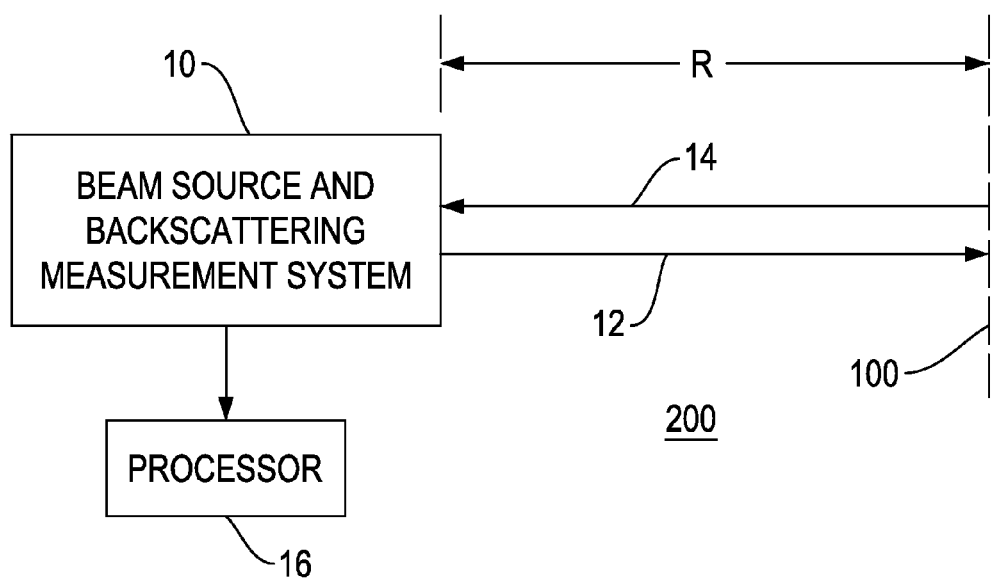
FIG. 1 is a top-level schematic view of a system used to remotely measure index of refraction fluctuations in accordance with the present invention.

Referring now to the drawings and more particularly to FIG. 1, a schematic view of a system used to remotely measure index of refraction fluctuations in accordance with the present invention is illustrated. At the heart of this system is a beam source and backscattering measurement system 10 used to both focus a light beam 12 at a focal plane 100 located a distance (or focal range) R from system 10 and measure the size of the backscattered beam image that arrives at system 10 along return beam path 14. Light beam 12 and return beam path 14 pass through a medium 200 (e.g., water, air, etc.) that is likely to experience index of refraction fluctuations. Medium 200 can be a single medium or multiple mediums (e.g., air and water) with a regular (e.g., flat) boundary between the two mediums. As would be understood by one of ordinary skill in the art, system 10 can be realized in a number of ways without departing from the scope of the present invention. By way of non-limiting example, one possible embodiment of system 10 will be described later herein.

For simplicity, the present invention will be explained for the case of a single focal range. However, it is to be understood that the method described herein can be extended for the measurement and use of data at multiple focal ranges where such multiple measurements could be made simultaneously or sequentially. Referring still to FIG. 1, a measurement of the beam size at the focal range R is an indirect measurement of the strength of index of refraction fluctuations in the propagation path between the output lens of system 10 and focal plane 100. Since observation of the beam at focal plane 100 by system 10 requires backscattering of the light by molecular and particulate scattering of the light and propagation back through the fluctuations along return beam path 14, the size of the beam image seen by system 10 increases further. If the outgoing beam nearly fills the output lens aperture of system 10, the irradiance seen by system 10's detector can be approximated by autoconvolving the irradiance in focal plane 100. In any case, the size of the detected beam represents an indirect measurement of the strength of index of refraction fluctuations in the path between the output lens of system 10 and focal plane 100. System 10 provides the size of the detected beam to a processor 16 where the present invention's methods are used to relate the size of the image to the strength, location in range, and size of the index of refraction fluctuations.

As the strength of the fluctuations increases, the size of the detected beam increases. If $I(x,y)$ is the irradiance measured in the detector plane with rectangular coordinates $(x,y)$, a measure of beam size can be the mean radius of the beam given by $$\bar{r} = \frac{\int\int dxdy I(x,y)\sqrt{(x-\bar{x})^2 + (y-\bar{y})^2}}{\int\int dxdy I(x,y)} \quad (1)$$

where $$\bar{x} = \frac{\int\int dxdy I(x,y)x}{\int\int dxdy I(x,y)} \text{ and } \bar{y} = \frac{\int\int dxdy I(x,y)y}{\int\int dxdy I(x,y)}.$$

Another possible measure of beam size is the mean square radius of the beam given by $$\overline{r^2} = \frac{\int\int dxdy I(x,y)((x-\bar{x})^2 + (y-\bar{y})^2)}{\int\int dxdy I(x,y)}. \quad (2)$$

When appropriate, $\bar{r}$ and $\overline{r^2}$ can be averaged over more than one laser pulse.

If beam 12 is a laser beam having a $TEM_{00}$ transverse mode structure, electric field intensity at the lens output of system 10 is given by $$E_-(\vec{r},0) = E_0 e^{-\alpha_0 \vec{r}^2} e^{-j\frac{k\vec{r}^2}{2R}} \quad (3)$$

where
j is the unit imaginary number, $j=\sqrt{-1}$;
k is the wave number, $$k = \frac{2\pi}{\lambda};$$

$\lambda$ is the light wave length in the medium;
$E_0$ is a complex constant;
$\vec{r} = x\hat{x} + y\hat{y}$;
$\hat{x}$ and $\hat{y}$ are orthogonal unit vectors in the $(x,y)$ plane of the lens;
R is the distance to the range gated focal plane 100; and $$\frac{1}{\sqrt{2\alpha_0}}$$

is the $e^{-1}$ radius of the beam irradiance $$I(\vec{r},0) \propto |E_-(\vec{r},0)|^2$$

at the lens output of system 10.

If medium 200 is free of index of refraction fluctuations, the electric field intensity $E_-$ will propagate to form a diffraction limited focused spot in the focal plane at the distance R from the lens. In this case, the irradiance $e^{-1}$ radius of the Gaussian shaped beam in the focal plane is given by $$r_{e^{-1}} = R\sqrt{\frac{2\alpha_0}{k}}.$$

However, in the presence of index of refraction fluctuations, $$\Delta n(\vec{r},z),$$

along the propagation direction, z, the size of the beam will increase in focal plane 100 or at z=R.

Prior to describing the processing approach of the present invention, an exemplary embodiment of system 10 will be described with reference to FIG. 2. A computer/controller 20 provides control signals to a trigger 22 that, in turn, generates an electronic pulse used to trigger operation of a laser 24. For the illustrated embodiment, it will be assumed that laser 24 generates a linearly polarized light pulse with a single $TEM_{00}$ spatial mode with good beam quality. In accordance with an additional control signal generated by computer 20, zoom optics 26 expand the diameter and adjust the convergence of the laser light beam to produce a focused spot of the desired diffraction limited size at a selected range R. The diameter of the light beam is selected to achieve the desired index of refraction measurement sensitivity over the selected range. The transmitted light beam further passes through a polarizing beamsplitter 28 that is configured to allow passage of the light beam. A quarter waveplate 30 converts the light into circularly polarized light. A lens 32 then focuses the transmitted light beam (referenced by arrowheads 12) through medium 200 and onto particle and molecular density scatterers contained with the focal region 102 of beam 12. Light that is scattered backward (referenced by arrowheads 14) is then collected by lens 32. To the extent that the polarization of the light is preserved in the scattering process, quarter waveplate 30 converts the returning backscattered light to linearly polarized light with a polarization that is rotated 90° relative to the state of the polarization generated by laser 24. Backscattered light with the 90° polarization rotation is deflected by beamsplitter 28 into imaging optics 34. Imaging optics 34 are configured by computer 20 to image the light through a shutter 36 and onto a detector array 38 with the desired magnification. A delay 40 controlled by computer 20 turns on shutter 36 to allow the passage of light that has traveled the requisite time to and from focal region 102. The open time for shutter 36 is set to pass light that is scattered within the focal range of region 102 and to block light that is scattered outside of the focal range. The image formed on detector array 38 is then provided to computer 20 where range and beam diameter are determined. Note that a number of elements of system 10 can be changed or modified without departing from the scope of the present invention. For example, the use of a broadband detector array and time gating could replace shutter 36 and detector array 38.

Existing index of refraction fluctuation studies illustrate the complex relationship between the irradiance $$I(\vec{r}, R)$$

and the spatial spectrum and strength of the fluctuations. See, for example, Andrews et al., *Laser Beam Propagation through Random Media* (SPIE PRESS, 1998). One approach for determining $$I(\vec{r}, R)$$

in accordance with the present invention uses a computer-implemented process described below. The process assumes a Kolmogorov spatial spectrum (see Andrews et al.) for the index of refraction fluctuations. An estimate is made of the inner ($l_0$) and outer ($L_0$) scales of the fluctuations.

Figure 2:
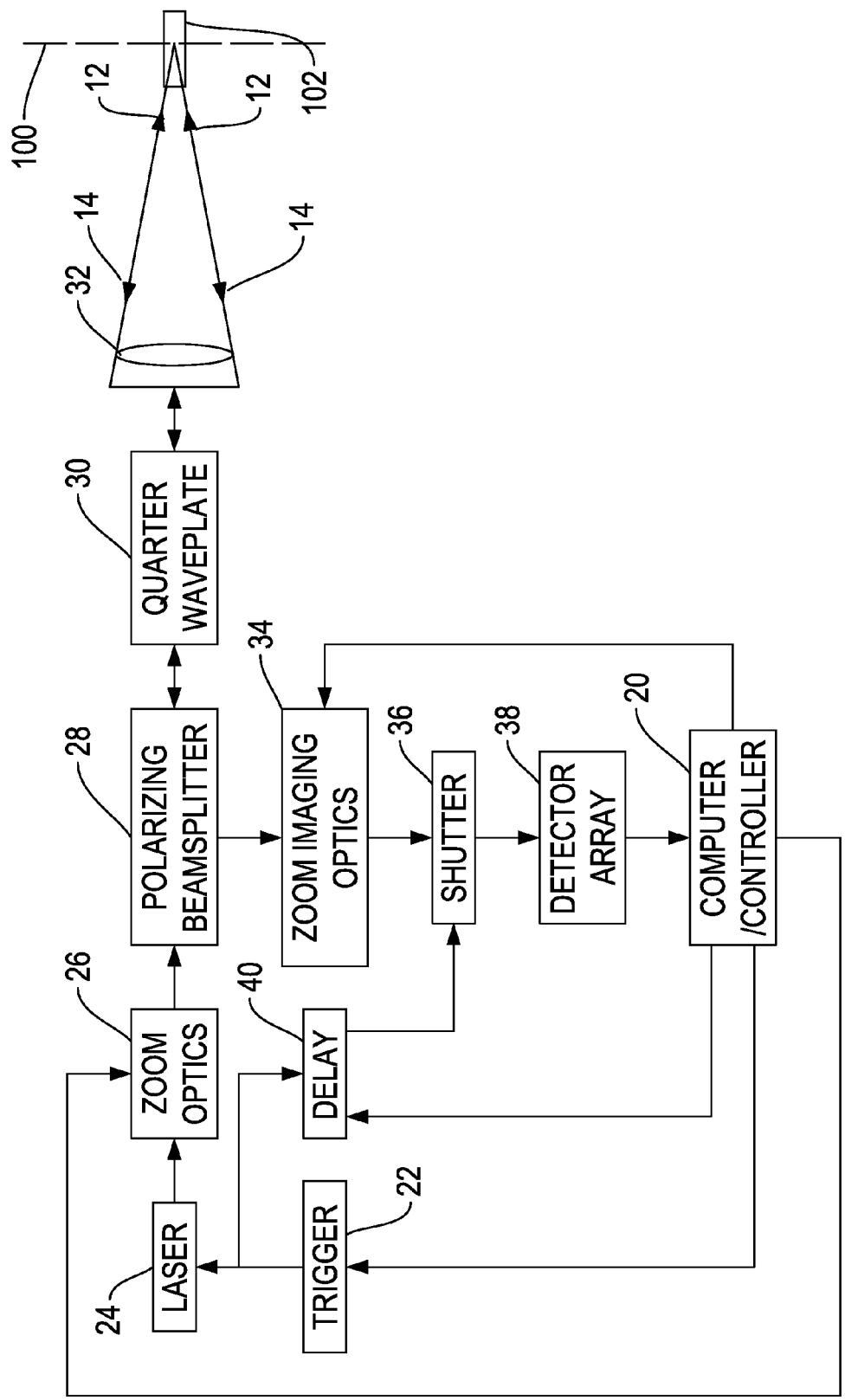
FIG. 2 is a schematic view of a beam source and backscattering measurement system in accordance with an embodiment of the present invention.
Figure 3:
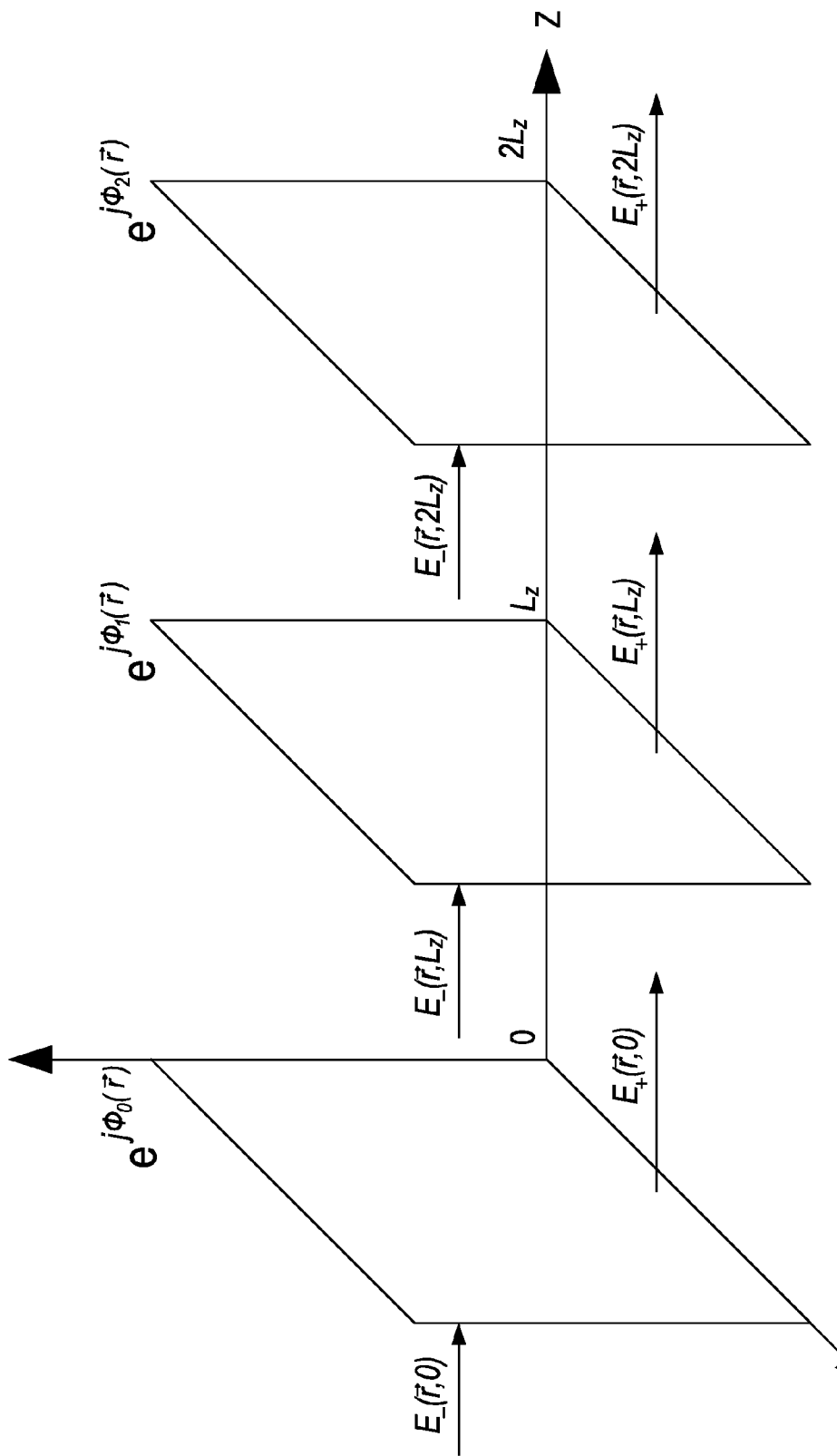
FIG. 3 is a diagrammatic view of a phase mask model of propagation through a medium with index of refraction fluctuations.

In terms of the system embodiment illustrated in FIG. 2, the propagation path between lens 32 and focal plane 100 can be broken into constant index of refraction slabs of length $L_z = L_0$. As described by Andrews et al., a phase mask with amplitude transmittance $$T_m = e^{j\phi_m(\vec{r})} \tag{5}$$

where $$\phi_m(\vec{r}) = k \int_{mL_z}^{(m+1)L_z} dz \Delta n(\vec{r}, z)$$

is used at the beginning of each slab to account for the index of refraction fluctuations within the slab. This situation is depicted in FIG. 3 for three slabs at $z=0, L_z, 2L_z$ with the input field being denoted above the arrow pointing to each slab, the phase mask being denoted above each slab, and the output field being denoted above the arrow pointing away from each slab.

Monte Carlo realizations of the $$\phi_m(\vec{r})$$

phases can be accomplished by using a Gaussian random number generator to create two-dimensional white noise. A two-dimensional Fourier transform can be used to convert the white noise to wavenumber space where the spatial spectrum is multiplied by a Kolmogory spectrum before an inverse transform is used to return to position space. An index of refraction structure constant $C_n^2$ is selected and the amplitude of the phase mask noise is adjusted until the variance of the phase mask fluctuations satisfies $$\sigma_\phi^2 = 0.275 C_n^2 L_0^{\frac{8}{3}} \tag{6}$$

where $\sigma_\phi^2$ is the mean square phase. The process described above can be used to generate independent realizations $$\phi_m(\vec{r})$$

of the phase masks.

Figure 4:
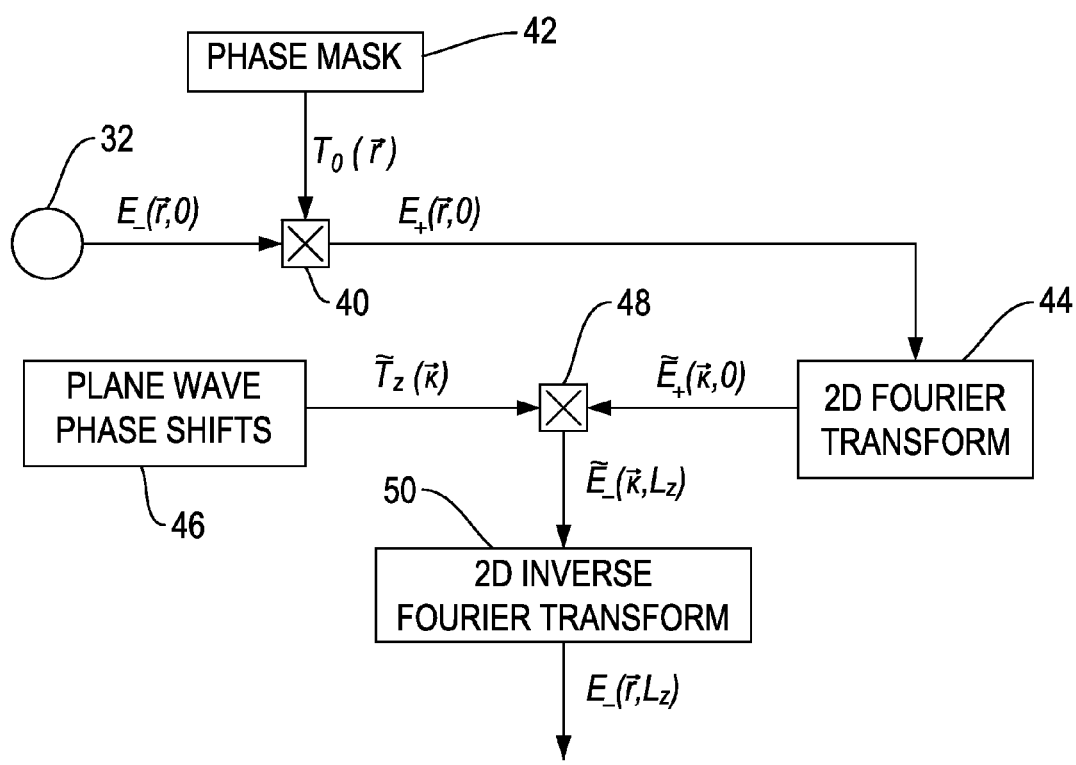
FIG. 4 is a block diagram illustrating the processing steps used to model propagation of electric field intensity at the lens output of the measurement system to the system's focal plane in accordance with the present invention.

With the phase mask amplitude transmittance determined as just described, the process used to model propagation of the field at the lens output to the focal plane is depicted in FIG. 4 for the first slab. As shown in FIG. 4, the electric field intensity $$E_-(\vec{r}, 0)$$

at the output of lens 32 is multiplied at 40 by the transmittance $$T_0(\vec{r})$$

of the first phase mask 42. The result $$E_+(\vec{r}, 0)$$

undergoes a two dimensional Fourier transform at 44 to $$\tilde{E}_+(\vec{\kappa}, 0),$$

wavenumber space to generate the plane wave amplitudes $$\vec{k} = \vec{\kappa} + \sqrt{k^2 - \kappa^2}\, \hat{z}$$

where $\vec{\kappa}$ is the projection of the wave vector $$\tilde{T}_z(\vec{\kappa}) = e^{jL_z\sqrt{k^2-\kappa^2}}, \quad (7)$$

in the (x,y) plane and $\hat{z}$ is a unit vector perpendicular to the (x,y) plane. The transmission function $$\tilde{E}_+(\vec{\kappa}, 0)$$

corresponding to the plane wave phase shifts 46 multiplies $$\tilde{E}_-(\vec{\kappa}, L_z)$$

at 48 to produce the wave number spectrum $$E_-(\vec{r}, L_z)$$

of the electric field at the end of the first slab. A two-dimensional inverse transform at 50 is used to generate the electric field intensity $$E(\vec{r}, R),$$

at the end of the first slab. This process is repeated for each slab until the electric field intensity, $$I(\vec{r}, R) = |E(\vec{r}, R)|^2$$

in the lens focal plane is determined. The relative irradiance $$I(\vec{r}, R)$$

is then determined.

An autocovolution of $$I_{DS}(\vec{r}, R) = \int d\vec{r}_0^2 I(\vec{r}_0, R) I(\vec{r} - \vec{r}_0, R). \quad (8)$$

is performed to determine the range gated irradiance $$I_{DS}(\vec{r}, R)$$

can then be used in Eq. 1 to determine the simulated mean radius $\bar{r}_S$. The mean radius is then compared with the experimentally determined mean radius. The structure constant, $C_n^2$, is changed accordingly and the propagation process is repeated until the measured and simulated mean radii are in good agreement. The final value of $C_n^2$ is used in Eq. 5 to determine the mean square phase $\sigma_\phi^2$ which constitutes another measurement of the index of refraction fluctuations in the propagation path. If desired, the process can be repeated to provide for ensemble averaging of the simulated beam size.

The above-described process can also be repeated for a longer focal range. The simulation process is repeated using the structure constant determined to characterize the first focal range and as a starting point for modeling the region between the two focal ranges. The search process is repeated for a range between the focal planes until $C_n^2$ and $\sigma_\phi^2$ are determined for the region between the two focal planes. This process can be repeated for any number of ranges that can be achieved, within the limits imposed by attenuation of the light within the propagation medium and the laser power level, to form $C_n^2$ and $\sigma_\phi^2$ range images of the strength of the index of refraction fluctuations.

It will be understood that many additional changes in the details, materials, steps and arrangement of parts, which have been herein described and illustrated in order to explain the nature of the invention, may be made by those skilled in the art within the principle and scope of the invention as expressed in the appended claims.

What is claimed is:

1. A method of remotely measuring fluctuations in a medium's index of refraction, comprising the steps of:
   focusing, from a first location, a first beam of optical energy at a focal plane located at a second location in a medium of interest wherein a second beam of optical energy is backscattered towards said first location;
   receiving said second beam of optical energy at said first location; and
   determining a change in size of said second beam wherein said change is an indirect measurement of strength of fluctuations in the medium's index of refraction.

2. A method according to claim 1, wherein said first beam comprises a laser beam pulse having a length that is less than a distance between said first location and said second location.

3. A method according to claim 2, wherein said first beam comprises a laser beam pulse having a $TEM_{00}$ transverse mode structure.

4. A method according to claim 1, wherein said step of determining includes a step of determining irradiance of said second beam.

5. A method according to claim 4, wherein said step of determining comprises a step of determining a mean radius of said second beam.

6. A method according to claim 4, wherein said step of determining comprises a step of determining a mean square radius of said second beam.

7. A system for remotely measuring fluctuations in a medium's index of refraction, comprising:
   a light source at a first location for focusing a first beam of optical energy at a focal plane located at a second location in a medium of interest wherein a second beam of optical energy is backscattered towards said first location;
   a detector at said first location for generating an image of said second beam at said first location; and
   a processor coupled to said detector for determining irradiance associated with said image, wherein said irradiance is indicative of size of said second beam, and wherein said size is indicative of strength of fluctuations in the medium's index of refraction.

8. A system as in claim 7, wherein said light source includes a laser, and wherein said first beam comprises a laser beam pulse having a length that is less than a distance between said first location and said second location.

9. A system as in claim 7, wherein said light source includes a laser, and wherein said first beam comprises a laser beam pulse having a $TEM_{00}$ transverse mode structure and having a length that is less than a distance between said first location and said second location.

10. A system as in claim 7, wherein said processor uses said irradiance to determine a mean radius of said second beam.

11. A system as in claim 7, wherein said processor uses said irradiance to determine a mean square radius of said second beam.

12. A system for remotely measuring fluctuations in a medium's index of refraction, comprising:
   a laser capable of providing a light beam;
   a beam splitter having an input joined to receive the light beam from said laser, a port capable of providing output of a beam received at the input and further being capable of receiving a backscatter light beam, and an output capable of providing the backscatter light beam received at the port;
   a lens joined to said beam splitter port for focusing said beam splitter port output to a remote location located at a distance from said lens whereby said beam splitter port output causes creation of a backscatter light beam through interaction with the medium, said backscatter light beam returning through said lens to said beam splitter port, and the light beam being provided as a pulse of shorter length than the distance between said lens and the remote location;
   a detector joined to said beam splitter output for detecting a change in size of the backscatter light beam; and
   a processor joined to the detector and capable of providing a measure fluctuations in the medium's index of refraction.

13. The apparatus of claim 12, further comprising:
   a quarter waveplate interposed between said beam splitter and said lens, said quarter waveplate being capable of receiving the beam splitter port output and providing a circularly polarized output, said quarter waveplate being capable of receiving the backscatter light beam from said lens and providing a rotated polarization of the backscatter light beam with respect to said circularly polarized output;
   wherein said beam splitter is a polarizing beam splitter in which light received at the port having a rotated polarization is provided to the beam splitter output.

14. The apparatus of claim 12, further comprising a shutter interposed between said beam splitter and said detector and joined to said processor, said shutter being controlled by said processor to prevent backscatter light beam from times other than those consistent with backscatter light from the remote location from reaching said detector.

15. The apparatus of claim 12, further comprising a trigger joined between said laser and said processor, said processor being capable of transmitting a control signal to said trigger, said trigger being joined to activate said laser in order to pulse the light beam for a predetermined duration.

* * * * *